May 23, 1972 L. H. SHOESMITH Plant Pat. 3,194

CHRYSANTHEMUM PLANT (ONWARD)

Filed Oct. 5, 1970

INVENTOR.
LEONARD H. SHOESMITH

BY Rummler & Snow
ATTYS.

United States Patent Office

Plant Pat. 3,194
Patented May 23, 1972

3,194

CHRYSANTHEMUM PLANT (ONWARD)

Leonard H. Shoesmith, Westfield-Woking, Surrey, England, assignor to Pan-American Plant Company, West Chicago, Ill.

Filed Oct. 5, 1970, Ser. No. 78,313
Int. Cl. A01h *5/00*
U.S. Cl. Plt.—79 1 Claim

ABSTRACT OF THE DISCLOSURE

A new variety of chrysanthemum plant of standard type having large blooms of a rich bronze coloring that do not sunburn, a nine weeks year-around response to photoperiod culture, a vigorous growth habit during all seasons, and good retention of coloring under high temperature.

BACKGROUND OF THE NEW PLANT

My new variety of chrysanthemum plant was discovered by me while engaged in extensive breeding efforts since 1967 at West Chicago, Ill., seeking new and improved varieties of chrysanthemums for standard greenhouse culture. The parentage of the new plant is unkown, the plant having been selected by me from among a multitude of seedlings resulting from random crosses and chosen for propagation and testing because of the unique coloring of its bloom, which appeared to resist sunburn, and the large size of the flower.

Asexual reproduction of this plant by vegetative cuttings under greenhouse culture at West Chicago, Ill., showed the plant to have a vigorous, sturdy and upright growth habit, a very large flower when the plant is disbudded, and a consistent nine week photoperiod response during all times of the year. This plant is now being propagated in commercial quantities, by vegetative procedures, at West Chicago, Ill., and at Cortez, Fla., and all of the before mentioned features have been found to hold true from generation to generation and to be firmly fixed.

DESCRIPTION OF THE DRAWINGS

This new variety of chrysanthemum plant is illustrated by the accompanying drawing which shows the color characteristics of the flower as nearly true as it is reasonably possible to obtain through conventional photographic procedures, and which shows by pen and ink drawings the configuration of typical specimens of the leaves.

DESCRIPTION OF THE NEW PLANT

Figure 1:
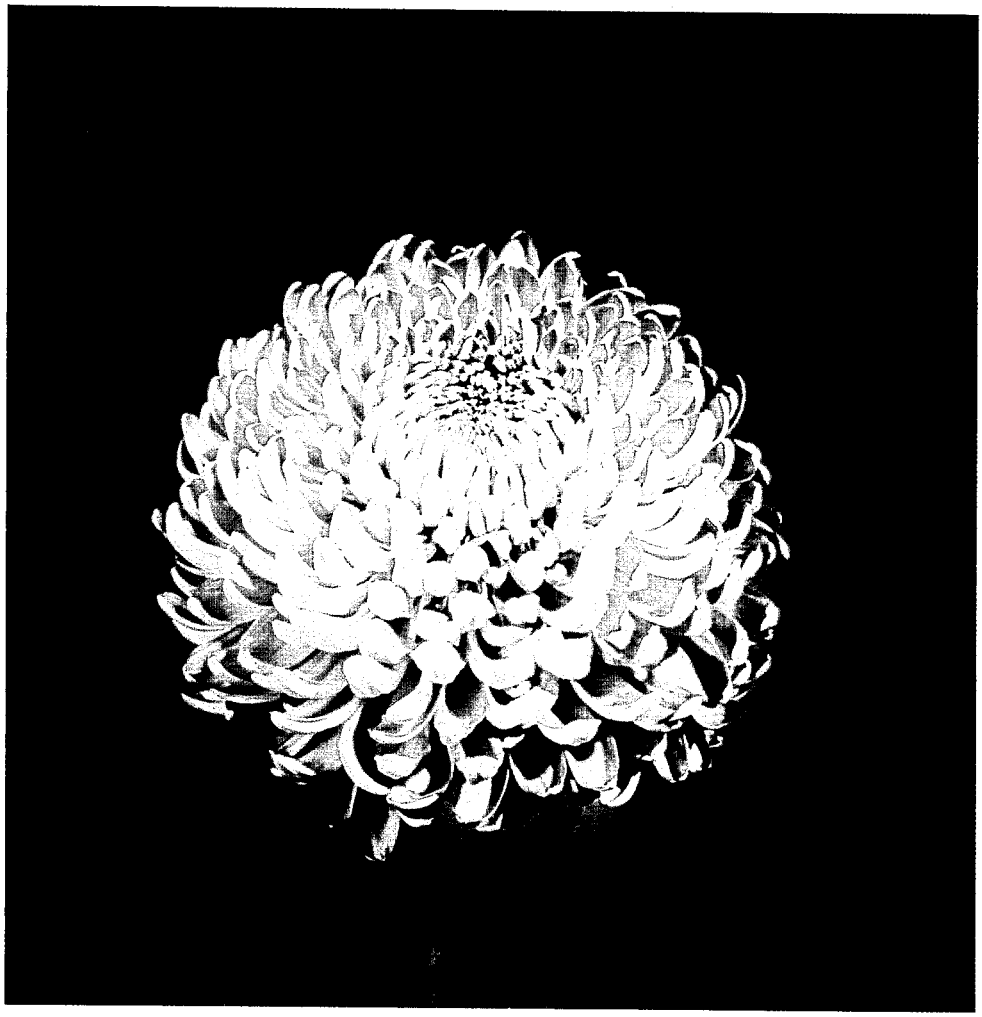
Figure 2:
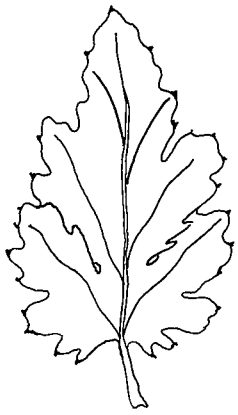
Figure 3:
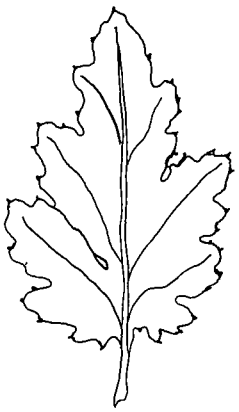

The following is a detailed description of the new variety of chrysanthemum plant with color descriptions according to the Horticultural Colour Chart issued by the British Colour Council.

*The plant*

Origin: Seedling
Parentage: Unknown. This seedling selected from many resulting from random crosses.
Classification:
*Botanic.*—*Chrysanthemum morifolium.*
*Commercial.*—Standard.
Form: Standard.
Height: Tall, 3 feet.
Growth: Vigorous, strong, sturdy and upright.
Foliage: Sparse in quantity. 13 leaves per 3 feet of stem.
*Leaf size.*—Approximately 5½ inches long x 3½ to 4 inches wide.

*Shape.*—Deeply lobed lanceolate and serrated.
*Texture.*—Tomentose and smooth.
*Color.*—Upper side—Spinach Green 960/1. Under side—Spinach Green 960.
*Ribs and veins.*—Pinnate.
*Petioles.*—1¼ to 1½ inches long.

*The bud*

Form: Round with flat top—cup shaped with low center. Diameter: ¾ inch; depth: ¼ to ½ inch.
Opening rate: Slowly—3 to 4 weeks depending on season.
Color: When sepals first divide: Green. When petals begin to unfurl: Green with dull gold cast.
Sepals: Spear-shaped and stand up. Color: Inside—Spinach Green. Outside—Spinach Green.
Calyx: Flat in shape.
*Size.*—Insignificant.
*Aspect.*—Smooth.
Peduncle: Erect, 2 inches long and slightly tomentose. Color: Scheeles Green 860.

*The flower*

Blooming characteristics: Photoperiod responsive with nine week response at any time of the year.
Size of bloom: Large. Approximately 6 inches in diameter and 1½ inches in depth when disbudded.
Borne: Singly when disbudded. Otherwise in raceme cluster.
Shape: Cup shaped with low center when bloom first opens. Form changes slightly as bloom matures—petals curve downwardly.
Petalage: Numerous in quantity, in the full flower, in composite arrangement.
*Form.*—Ray floret, smooth and rounded at ends.
*Color.*—Inside of petal—Jasper Red 018.
Reverse side of petal—Barium Yellow 503.
*Texture.*—Soft; aspect: satiny.
Peduncle: Sturdy and upright—about 2 inches long. Color: Scheeles Green 860.
Discoloration after full bloom: None. Flower color becomes lighter with high temperature.
Persistence: Rays hang on and dry.
Lasting quality: Long lasting on the plant and as a cut flower.

*Reproductive organs*

Stamens:
*Anthers.*—Many in disc arrangement, ⅛ inch long.
*Filaments.*—⅛ inch long. Color: Yellow.
*Pollen.*—Color: Yellow.
Pistils: One on each Ray floret—¼ inch long.
Stigmas: Color: Yellow.
Characteristics of ovaries: Insignificant.

The principal distinctions of my new variety of chrysanthemum plant appear to be in the improved bronze type of flower coloring, the large size of the flower, the resistance to sunburn, the vigorous, strong and upright growth habit, and the uniform response of the plant during all times of the year.

I claim:

1. A new and distinct variety of chrysanthemum plant, substantially as herein shown and described, characterized by the unique generally bronze coloring of its very large flower, its uniform nine week response and strong, upright growth habit, and its ability to be flowered at any time during the year.

No references cited.

ROBERT E. BAGWILL, Primary Examiner